United States Patent
Vögele et al.

(10) Patent No.: US 6,318,365 B1
(45) Date of Patent: Nov. 20, 2001

(54) PROCESS FOR SWITCHING THE INSPIRATION OR EXPIRATION PHASE DURING CPAP THERAPY

(75) Inventors: Harald Vögele, München; Jutta Griebel, Pflaumdorf; Stefan Madaus, München, all of (DE)

(73) Assignee: Map Medizintechnik für Arzt und Patient GmbH (DE)

( * ) Notice: Subject to any disclaimer, the term of this patent is extended or adjusted under 35 U.S.C. 154(b) by 0 days.

(21) Appl. No.: 09/355,180

(22) PCT Filed: Feb. 17, 1998

(86) PCT No.: PCT/EP98/00906

§ 371 Date: Sep. 9, 1999

§ 102(e) Date: Sep. 7, 1999

(87) PCT Pub. No.: WO98/35715

PCT Pub. Date: Aug. 20, 1998

(30) Foreign Application Priority Data

Feb. 17, 1997 (DE) .............................. 197 06 092

(51) Int. Cl.$^7$ .................................. A61M 16/00
(52) U.S. Cl. ................. 128/204.23; 128/204.18
(58) Field of Search ........... 128/204.18, 204.21, 128/204.22, 204.23, 204.26, 206.21

(56) References Cited

U.S. PATENT DOCUMENTS

| | | | |
|---|---|---|---|
| 5,503,146 | * | 4/1996 | Froehlich et al. ............ 128/204.23 |
| 5,551,419 | * | 9/1996 | Froehlich et al. ............ 128/204.23 |
| 5,823,187 | * | 10/1998 | Estes et al. .................. 128/204.23 |
| 5,845,636 | * | 12/1998 | Gruenke et al. ............. 128/204.23 |
| 5,865,173 | * | 2/1999 | Froehlich .................... 128/204.23 |
| 5,904,141 | * | 5/1999 | Estes et al. .................. 128/204.23 |
| 5,970,975 | * | 10/1999 | Estes et al. .................. 128/204.23 |

FOREIGN PATENT DOCUMENTS

| | | | |
|---|---|---|---|
| 0 606 687 A2 | 7/1994 | (EP) | ............ A61M/16/00 |
| 0 656 216 A2 | 6/1995 | (EP) | ............ A61M/16/00 |
| 0 714 670 A2 | 6/1996 | (EP) | ............ A61M/16/00 |
| 0 722 747 A2 | 7/1996 | (EP) | ............ A61M/16/00 |
| WO 93/08857 | 5/1993 | (WO) | ............ A61M/16/00 |

\* cited by examiner

Primary Examiner—John G. Weiss
Assistant Examiner—Teena Mitchell
(74) Attorney, Agent, or Firm—George W. Rauchfuss, Jr.; Ohlandt, Greeley, Ruggiero & Perle, LLP

(57) ABSTRACT

A method of changing to the inhalation or exhalation phase in the CPAP therapy is provided. By means of a first, high threshold value and a second, low threshold value, nonspecific influences on the first derivative of the gas flow curve are suppressed in the respective breathing phase and the transition to the respective next gas phase is determined with high sensitivity. The advantages of the invention are in a higher precision of the changing operation and in a greater safety for the patient.

10 Claims, 3 Drawing Sheets

PROCESS FOR SWITCHING THE INSPIRATION OR EXPIRATION PHASE DURING CPAP THERAPY

Figure 1:
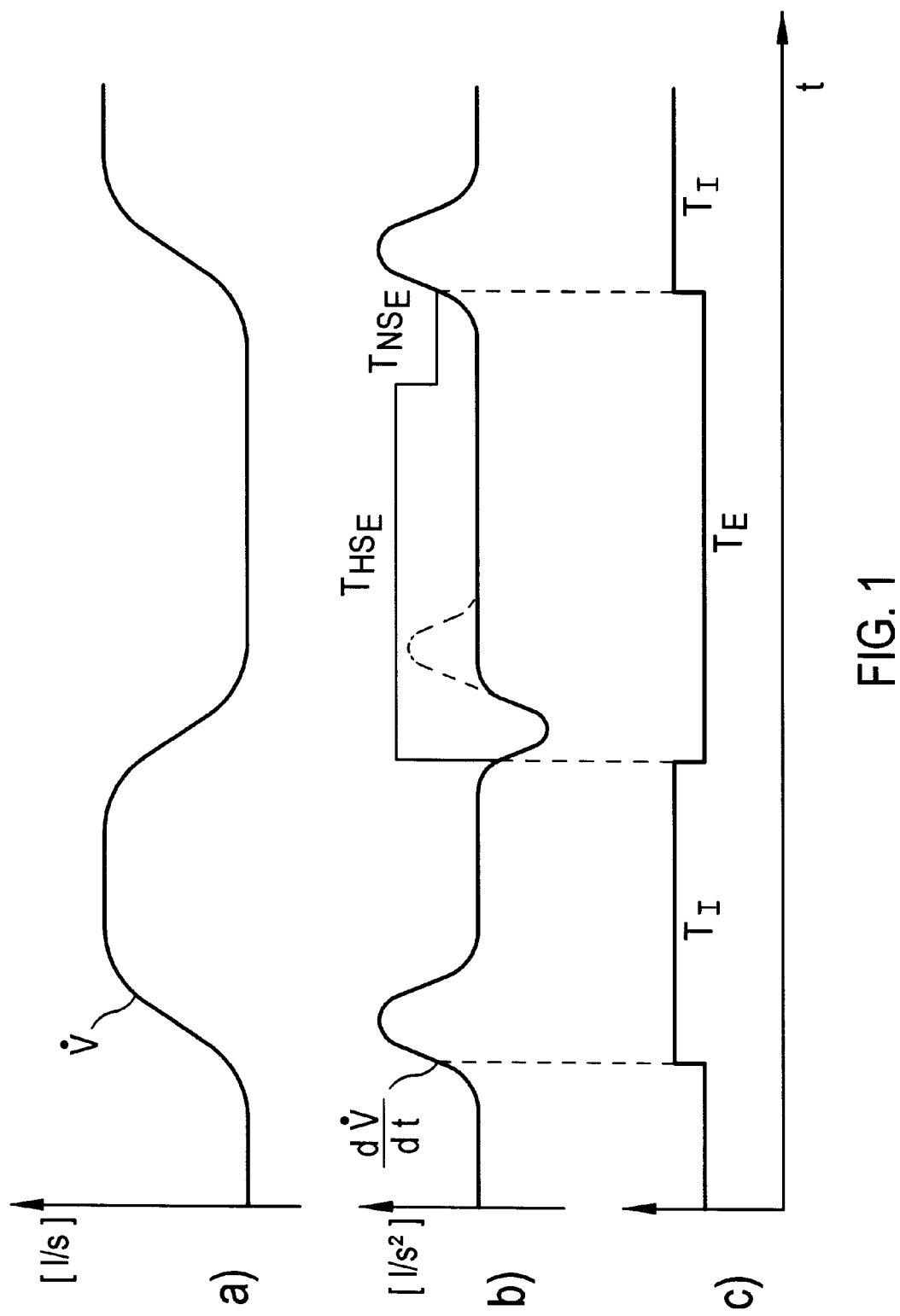

The invention relates to a method of switching or changing from the inhalation phase to the exhalation phase or vice versa in the CPAP (continuous positive airways pressure) therapy, in which a positive air pressure is continuously exerted onto the airways (CPAP therapy).

The CPAP therapy serves for pneumatically supporting the larynx by continuously supplying a positive air pressure onto the airways. The pressure level is individually adjusted to the patient. The invention is used in a varied CPAP method wherein the exhalation takes place at a lower pressure level than the inhalation. This has the advantage that the patient does not have to exhale against the high pressure level. It is of great importance for the patient's safety that the adjustment of the different pressure levels during the transition from the inhalation phase to the exhalation phase and vice versa takes place with high precision.

In the state of the art, usually the respiratory gas flow from and to the patient is measured and differentiated with respect to time (first derivative) for obtaining a more distinct transition between the inhalation and exhalation phases. The differential functions of the flanks of the gas flow curve are compared with threshold values indicating a transition to the respective other breathing phase. However, the patient's respiratory gas flow may comprise deviations; furthermore, influences of the patient's pulse may have an effect on the gas flow. This may result in an overshooting of the first differential function, wherein the threshold value for changing to the other breathing phase is achieved prior to the required time so that it is changed to the other pressure level and the patient's safety may be jeopardized.

A method of changing to the inhalation phase or exhalation phase in the CPAP therapy is known from EP-A2-0 656 216. In this method, the motor speed and current consumption of a generator for supplying a patient with air is controlled and an operation signal is derived for the purpose of determining the inhalation and exhalation phases. A signal representative of the gas flow to the patient is derived from the operation signal. The flow signal d"flow"/dt differentiated with respect to time is compared with a first and a second threshold value and the change in the breathing phase is derived therefrom.

The invention is based on the problem of providing an improved method for changing to the inhalation or exhalation phase in the CPAP therapy, wherein the transition to the inhalation or exhalation phase is recognized with high precision and the patient's safety is increased.

The problem is solved with the features of the claims.

According to the invention, the solution is based on the following principal concepts.

The first derivative of a respiratory gas flow curve from and to the patient is compared with two subsequent threshold values for the variation of the first derivative. The first threshold value is higher and therefore more insensitive. Deviations, which often occur at the beginning of a breathing phase, cannot reach said high threshold value and thus trigger any erroneous change of a pressure level in the CPAP therapy. Subsequent to the high threshold value, a low threshold value, which therefore is more sensitive, is set for the purpose of determining the transition to the next breathing phase with high precision. The change to the other breathing phase takes place when the first derivative has reached the second threshold value.

In the case of forced breathing, the high threshold may also be exceeded, which is the reason why spontaneous breathing is possible at any time.

In a specific embodiment of the invention, the time history of the gas flow in the exhalation phase is sampled in at least one sequence of three sampling values in addition to the comparison with the second, low value. If in such a sequence the condition is fulfilled that the second and the third sampling values exceed the respective preceding sampling values by a predetermined amount $\Delta$, the change to the inhalation phase occurs at the third sampling value; if this change-over does not occur, the change to the inhalation phase is triggered by said comparison of the first derivative with the low threshold value.

If none of the two aforementioned changing operations to the inhalation phase is triggered, the change-over occurs on account of a limiting time switching operation, e.g. at the latest after 3 to 4 s for the exhalation phase.

The advantages of the invention reside both in a low susceptibility to trouble and in a high precision during changing to the inhalation or exhalation phase in the CPAP therapy.

In the following, the invention is explained in more detail by means of the drawings.

Figure 2:
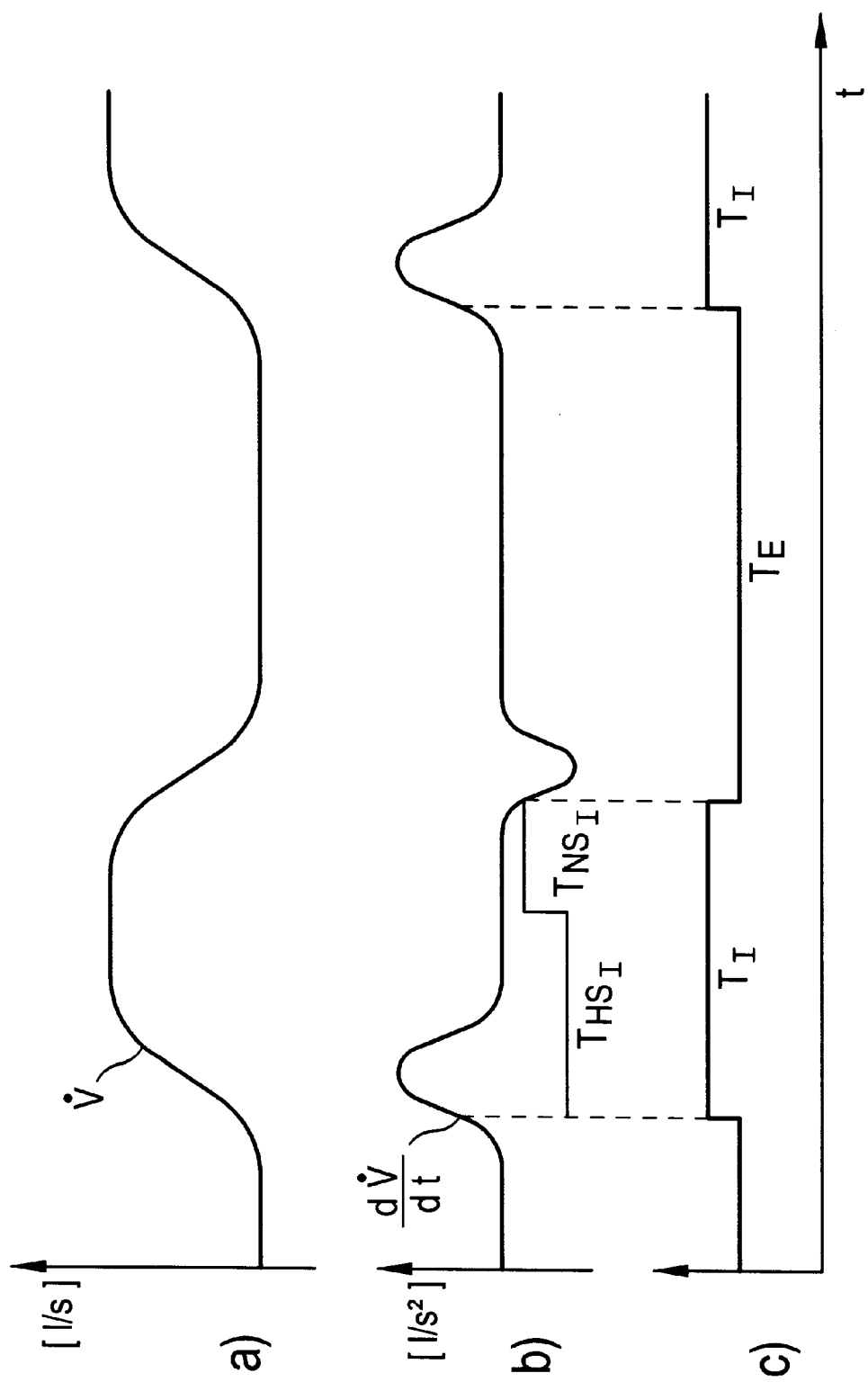
Figure 3:
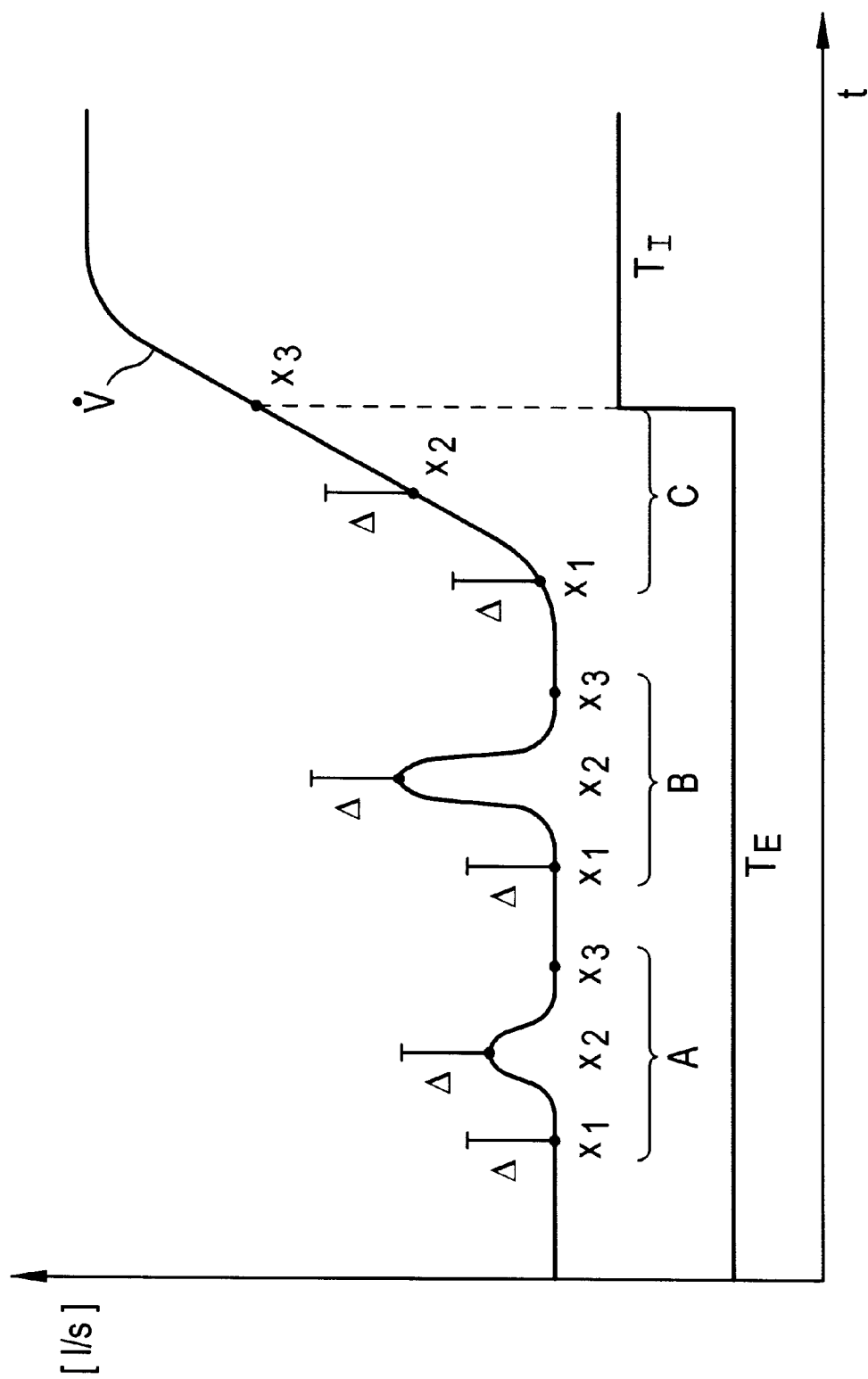

FIG. 1 shows diagrams for illustrating the method according to the invention during changing from the exhalation phase to the inhalation phase, FIG. 2 shows diagrams for illustrating the method according to the invention during changing from the inhalation phase to the exhalation phase, and FIG. 3 shows a further embodiment of the method according to the invention.

The diagram according to FIG. 1(a) shows the time history of the respiratory gas flow curve $\dot{V}$ (e.g. in l/s). FIG. 1(b) shows the first derivative of the respiratory gas flow curve with respect to time $d\dot{V}/dt$; and FIG. 1(c) shows an enlarged section of the sequence of inhalation phase (inspiration) and exhalation phase (expiration) $T_I$ and $T_E$, respectively, which sequence has been derived from the first derivative.

FIG. 1(b) illustrates the transition from the exhalation phase to the inhalation phase with respect to two threshold values $HS_E$ and $NS_E$. Following the change to the exhalation phase $T_E$ a high threshold value $HS_E$ is set for triggering the next change to the inhalation phase. It can be recognized that a possible overshooting (broken line) does not reach the threshold value HSE and thus cannot trigger any erroneous change. After a period of time $T_{HS(E)}$, which preferably is 1.25 times the duration of the inhalation phase $T_I$, a low threshold value $NS_E$ is set. In this range, where the transition to the other breathing phase takes place, the low, more sensitive threshold value guarantees an exact determination of the transition time. For the purpose of avoiding an insensitivity of a respective device that lasts too long, the duration of the high threshold $T_{HS(E)}$ in the exhalation phase $T_E$ is limited to approximately 3 seconds.

Besides, the inhalation is prevented at the beginning of the exhalation phase for a duration of approximately 1 second.

The low threshold value $NS_E$ in the exhalation phase is only set in the case of a negative value of the gas flow relative to a previous calibration of the system to the gas flow "zero". If this is not the case, the taking effect of the threshold value NS is deferred by 100 ms each time, until a negative value is determined.

In FIG. 2(a), the time history of the respiratory gas flow curve $\dot{V}$ is represented; FIG. 2(b) shows the first derivative of the respiratory gas flow curve and FIG. 2(c) shows the sequence of the inhalation and the exhalation phases which has been derived from the first derivative.

FIG. 2 depicts the transition from the inhalation phase to the exhalation phase with respect to the threshold values HSI and $NS_I$. The high threshold value $HS_I$ means the permission of a deviation from the first derivative towards lower values than at the second threshold value NSI. Hence, after the beginning of the inhalation phase the change-over is more insensitive to deviations in the intensity of the first derivative towards lower values which could initiate the change to the exhalation phase. As in FIG. 1, the smaller deviation of the low threshold value from the first derivative results in an increased sensitivity to a drop of the curve of the first derivative, which indicates the transition to the exhalation phase. The low threshold value $NS_I$ in the inhalation phase is only set in the case of a positive value of the gas flow relative to a previous calibration of the system to the gas flow "zero". If this is not the case, the taking effect of the threshold value NS is deferred by 100 ms each time, until a positive value is determined.

FIG. 3 shows an embodiment according to the invention in which in addition to the method represented in FIG. 1, the gas flow curve $\dot{V}$ is sampled in a sequence of at least three sampling values $X_1$, $X_2$ and $X_3$ in the exhalation phase during the comparison of the first derivative with the second, low threshold value $NS_E$. For the change to the inhalation phase $T_I$, the condition must be fulfilled that in three sampling values $X_1$ to $X_3$, the second and third sampling values $X_2$ and $X_3$, respectively, exceed the preceding sampling values $X_1$ and $X_2$, respectively, by a predetermined amount $\Delta$; i.e. the two conditions $X_1+\Delta<X_2$ and $X_2+\Delta<X_3$, wherein $\Delta$ is an appropriately predetermined value. It can be deduced from FIG. 3 that only the last sequence C of $X_1$ to $X_3$ values being on the flank of the inhalation gas flow fulfils this condition. In the first sequence A of $X_1$ to $X_3$ values, already the $X_2$ value does not meet the aforementioned criterion; and in the second sequence B of $X_1$ to $X_3$ values, the criterion is fulfilled as regards the value $X_2$ but not as regards $X_3$. It is thus possible to recognize short-term deviations which, for instance, may be due to the patient's pulse and appear relatively large in the first derivative of the gas flow curve $\dot{V}$, so that the change to the inhalation phase is not triggered by these incorrect signals. By means of a temporal limitation of the exhalation phase of e.g. 3 to 4 s, it is thereafter changed in any case to the inhalation phase irrespective of the triggering of the change-over by the gas flow signal or by the derivative of the gas flow signal.

This method leads to the change to the inhalation phase also, for instance, in such cases in which the respiration is so shallow that the values of the gas flow curve in the inhalation phase do not reach the low threshold value $NS_E$.

The sampling values are to be separated by intervals each of which is longer than the raising time of a pulse wave of the patient; preferably the intervals between the sampling values are 200 to 300 ms each.

The invention also relates to a device which can perform the method steps shown in FIGS. 1 to 3.

What is claimed is:

1. A method for changing to the inhalation or exhalation phase ($T_I$ and $T_E$, respectively) with a CPAP device, during a CPAP therapy of a patient, the steps comprising:

differentiating a respiratory gas flow (V) from and to the patient with respect to time;

changing to a respective breathing phase (i.e. inhalation or exhalation) wherein after changing to a respective breathing phase;

comparing a first derivative (dV/dt) of the gas flow (V) with a first, high threshold value ($HS_E$, $HS_I$) and then a second, low threshold ($NS_E$, $NS_I$) for a variation of the first threshold;

changing to a respective other breathing phase occurs when the first derivative has reached the second threshold value ($NS_E$, $NS_I$);

comparing the first derivative with the second, low threshold value ($NS_E$) in the exhalation phase;

sampling a time history of the respiratory gas flow (V) in a sequence of at least three sampling values ($X_1$, $X_2$, $X_3$);

changing to the inhalation phase at $X_3$ if the following two conditions $X_1+\Delta<X_2$ and $X_2+\Delta<X_3$ $\Delta$=predetermined increment are fulfilled, unless the change has already occurred earlier on account of the comparison of the first derivative with the low threshold value ($NS_E$).

2. The method according to claim 1, wherein the sampling values ($X_1$, $X_2$ and $X_3$) are separated by intervals each of which is longer than a raising time of a pulse wave of the patient.

3. The method according to claim 2, wherein the intervals between the sampling values ($X_1$, $X_2$ and $X_3$) are from 200 to 300 ms each.

4. The method according to claim 1 wherein the duration ($T_{HS}$) of the comparison of the first derivative with the high threshold value ($HS_E$, $HS_I$) is longer than the duration of the comparison with the low threshold value ($NS_E$, $NS_I$).

5. The method according to claim 4 wherein the following applies in the exhalation phase:

$T_I \leq T_{HS(E)} < 4s$.

6. The method according to claim 5 wherein.

$T_{HS(E)} \geq 1.25 \times T_I$.

7. The method according to claim 4 wherein the following applies:

$1.25 s \leq T_{HS(I)} < 3s$.

8. The method according to claim 1 wherein, at the beginning of the exhalation phase, inhalation is prevented for 1 second.

9. The method according to claim 1 wherein the low threshold value ($NS_I$) in the inhalation phase is only set in the case of a positive value of the gas flow (V), and otherwise the taking effect of the threshold value ($NS_I$) is deferred by 100 ms each time until a positive value of the gas flow (V) is determined.

10. The method according to claim 1 wherein the low threshold value ($NS_E$) in the exhalation phase is only set in the case of a negative value of the gas flow (V) and otherwise the taking effect of the threshold value ($NS_E$) is deferred by 100 ms each time until a negative value of the gas flow (V) is determined.

* * * * *